United States Patent [19]
Burckhardt et al.

[11] Patent Number: 4,748,178
[45] Date of Patent: May 31, 1988

[54] 5-(PYRIDYLOXY- OR PYRIDYLTHIO-PHENYL)CARBAMOYL BARBITURIC ACID DERIVATIVES

[75] Inventors: Urs Burckhardt, Basel; Jean J. Gallay, Magden; Manfred Kühne, Pfeffingen, all of Switzerland

[73] Assignee: Ciba-Geigy Corporation, Ardsley, N.Y.

[21] Appl. No.: 829,589

[22] Filed: Feb. 13, 1986

Related U.S. Application Data

[63] Continuation-in-part of Ser. No. 788,087, Oct. 15, 1985, abandoned, which is a continuation of Ser. No. 641,092, Aug. 15, 1984, abandoned.

[30] Foreign Application Priority Data

Aug. 19, 1983 [CH] Switzerland ................. 4535/83
Jul. 20, 1984 [CH] Switzerland ................. 3526/84

[51] Int. Cl.$^4$ ................. A61K 31/495; C07D 401/10
[52] U.S. Cl. ................. 514/270; 544/225; 544/226; 544/300
[58] Field of Search ................. 544/300, 225, 226; 514/270

[56] References Cited

U.S. PATENT DOCUMENTS

| 3,961,061 | 6/1976 | Kramer et al. | 544/301 |
| 4,229,454 | 10/1980 | Beriger | 544/301 |
| 4,239,762 | 12/1980 | Kramer et al. | 544/300 |
| 4,283,444 | 8/1981 | De Sousa et al. | 544/300 |
| 4,399,280 | 8/1983 | De Sousa et al. | 544/301 |
| 4,503,100 | 3/1985 | De Sousa | 514/271 |
| 4,602,912 | 7/1986 | De Sousa et al. | 544/300 |

FOREIGN PATENT DOCUMENTS

| 7541 | 2/1980 | European Pat. Off. | 514/270 |
| 105029 | 4/1984 | European Pat. Off. | 544/301 |
| 167491 | 1/1986 | European Pat. Off. | 544/300 |
| 2126582 | 3/1984 | United Kingdom | 514/270 |
| 2145087 | 3/1985 | United Kingdom | 514/270 |
| 2152047 | 7/1985 | United Kingdom | 514/270 |
| 2171099 | 8/1986 | United Kingdom | 514/270 |

OTHER PUBLICATIONS

Burckhardt et al., CA103-178271k.
Kuehne et al., CA 105-60628g.

Primary Examiner—Robert Gerstl
Assistant Examiner—Cecilia Shen
Attorney, Agent, or Firm—Edward McC. Roberts; Meredith C. Findlay

[57] ABSTRACT

Novel phenylcarbamoylbarbituric acid derivatives of the general formula I

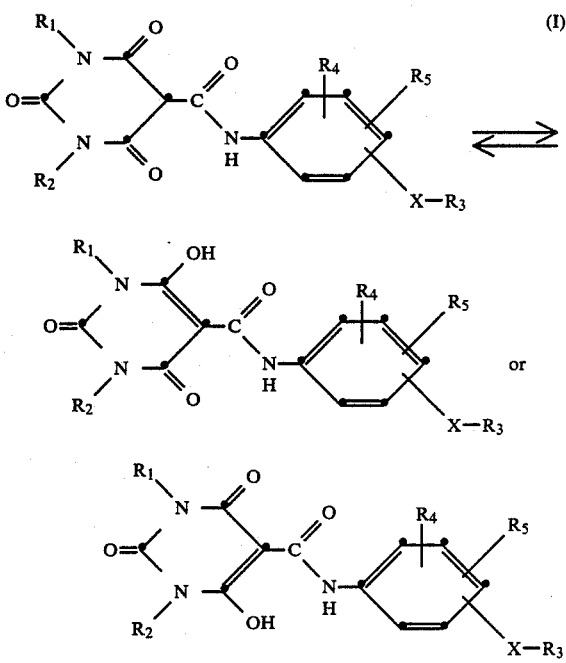

and tautomeric forms and salts thereof in which $R_1$ and $R_2$ independently of one another are $C_1$-$C_5$-alkyl, $C_1$-$C_3$-alkoxy, $C_3$-$C_6$-cycloalkyl, allyl or phenyl; $R_3$ is substituted or unsubstituted pyridyl as herein defined; and X is oxygen or sulfur; they possess anthelmintic activity. The active substances can be employed in conjunction with suitable carriers and further adjuncts for controlling zooparasitic helminths.

19 Claims, No Drawings

5-(PYRIDYLOXY- OR PYRIDYLTHIO-PHENYL)CARBAMOYL BARBITURIC ACID DERIVATIVES

The present invention relates to novel 5-phenylcarbamoylbarbituric acid derivatives having an anthelmintic action, to compositions containing these active compounds as the active substances and to the use of the active compounds or the compositions for the control of helminths, particularly nematodes and, to a certain extent, cestodes and trematodes in domestic animals and livestock, and especially in mammals.

The invention also relates to the preparation of the new active compounds and to the compositions containing them.

The novel compounds are those of tha general formula I

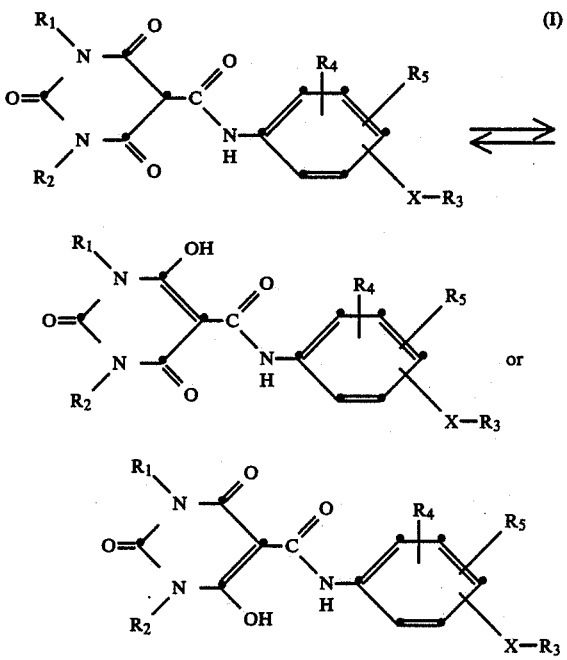

and tautomeric forms and salts thereof in which $R_1$ and $R_2$ independently of one another are $C_1$-$C_5$-alkyl, $C_1$-$C_3$-alkoxy, $C_3$-$C_6$-cycloalkyl, allyl or phenyl; $R_3$ is pyridyl, which is unsubstituted or monosubstituted to trisubstituted by substituents selected from the group consisting of halogen, cyano, thiocyano, isothiocyano, $C_1$-$C_5$-alkanoyl, $C_1$-$C_5$-alkyl, $C_1$-$C_5$-halogenoalkyl, $C_1$-$C_5$-halogenoalkoxy, $C_1$-$C_5$-alkoxy or benzyl; $R_4$ and $R_5$ independently of one another are hydrogen, halogen, $C_1$-$C_5$-halogenoalkyl, $C_1$-$C_5$-alkyl, $C_1$-$C_5$-alkoxy or $C_1$-$C_5$-alkylthio; and X is oxygen or sulfur.

Particularly to be mentioned are (i) compounds of the formula I in which the phenyl ring is substituted by the pyridyloxy group in a position meta or para to the carbamoyl group; especially in para position and (ii) compounds of the formula I in which the phenyl ring is substituted by a methoxy group in a position meta or para to the carbamoyl group.

Compounds of the formula I which are preferred are:
(1) those in which $R_1$ and $R_2$ independently of one another are $C_1$-$C_5$-alkyl, $C_1$-$C_3$-alkoxy, $C_3$-$C_6$-cycloalkyl or allyl; $R_3$ is pyridyl, which is unsubstituted or monosubstituted to trisubstituted by substituents selected from the group consisting of halogen, cyano, thiocyano, isothiocyano, $C_1$-$C_5$-alkanoyl, $C_1$-$C_5$-alkyl, $C_1$-$C_5$-halogenoalkyl, $C_1$-$C_5$-halogenoalkoxy, $C_1$-$C_5$-alkoxy and benzyl; $R_4$ is hydrogen, halogen, $C_1$-$C_5$-halogenoalkyl, $C_1$-$C_5$-alkyl, $C_1$-$C_5$-alkoxy; $R_5$ is hydrogen, halogen, $C_1$-$C_5$-halogenalkyl or $C_1$-$C_5$-alkyl; and X is oxygen or sulfur;

(2) those in which $R_1$ is $C_1$-$C_5$-alkyl or $C_1$-$C_3$-alkoxy; $R_2$ is $C_1$-$C_5$-alkyl, $C_1$-$C_3$-alkoxy, cyclopropyl or allyl; $R_3$ is pyridyl which is unsubstituted or mono- to trisubstituted by substituents selected from the group consisting of halogen, cyano, $C_1$-$C_5$-alkyl and $C_1$-$C_5$-halogenoalkyl; $R_4$ is hydrogen, halogen, $C_1$-$C_5$-alkyl or $C_1$-$C_5$-alkoxy; $R_5$ is hydrogen, halogen or $C_1$-$C_5$-alkyl; and X is oxygen; and metal salts or mono-, di- or trialkylamine salts thereof;

(3) those in which $R_1$ is methyl or methoxy; $R_2$ is methyl, ethyl, cyclopropyl or allyl; $R_3$ is (2)- or (5)-pyridyl, which is unsubstituted or mono- to trisubstituted by substituents selected from the group consisting of chlorine, fluorine, cyano, methyl, trifluoromethyl and 1,1-difluoro-2,2-dichloro-2-fluoroethyl; $R_4$ is hydrogen, chlorine, methyl, isopropyl or methoxy; $R_5$ is hydrogen, chlorine or methyl; and X is oxygen; and the Ca, Zn, Al, $Fe^{III}$ and triethylamine salts thereof and particularly those compounds in which $R_2$ is methyl, cyclopropyl or allyl;

(4) those in which $R_3$ is (2)-pyridyl which is unsubstituted or mono- to trisubstituted by substituents selected from the group consisting of chlorine, fluorine, cyano, methyl or trifluoromethyl and particularly those compounds in which $R_2$ is methyl, cyclopropyl or allyl;

(5) those in which $R_1$ is methyl or methoxy; $R_2$ is methyl; $R_3$ is (2)-pyridyl mono- or disubstituted by substituents selected from the group consisting of chlorine, fluorine and trifluoromethyl; $R_4$ is hydrogen, methyl, isopropyl or methoxy; $R_5$ is hydrogen or methyl and X is oxygen and particularly those compounds in which $R_4$ is hydrogen and $R_5$ is hydrogen and additionally, if $R_1$ is other than methoxy, $R_4$ is methoxy.

The following are preferred individual compounds: 1,3-dimethyl-5-[4-(3,5-dichloropyridyl-2-oxy)-phenylcarbamoyl]-barbituric acid, 1,3-dimethyl-5-[4-(5-trifluoromethylpyridyl-2-oxy)-phenylcarbamoyl]-barbituric acid, 1-methoxy-3-methyl-5-[4-(3,5-dichloropyridyl-2-oxy)-phenylcarbamoyl]-barbituric acid, 1,3-dimethyl-5-[4-(3-chloro-5-trifluoromethylpyridyl-2-oxy)-phenylcarbamoyl]-barbituric acid, 1-methoxy-3-methyl-5-[4-(3-chloro-5-trifluoromethylpyridyl-2-oxy)-phenylcarbamoyl]-barbituric acid, 1,3-dimethyl-5-[3-methoxy-4-(3,5-dichloropyridyl-2-oxy-)-phenylcarbamoyl]-barbituric acid, 1,3-dimethyl-5-[4-methoxy-3-(3-chloro-5-trifluoromethylpyridyl-2-oxy)-phenylcarbamoyl]-barbituric acid, 1,3-dimethyl-5-[4-methoxy-3-(3,5-dichloropyridyl-2-oxy)-phenylcarbamoyl]-barbituric acid and 1,3-dimethyl-5-[4-methoxy-3-(5-trifluoromethylpyridyl-2-oxy)phenylcarbamoyl]-barbituric acid, 1,3-dimethyl-5-[4-(5-chloro-3-fluoropyridyl-2-oxy)-phenylcarbamoyl]-barbituric acid and 1-methoxy-3-methyl-5-[4-(5-chloro-3-fluoropyridyl-2-oxy)-phenylcarbamoyl]-barbituric acid. The most preferred compound is 1,3-dimethyl-5-[4-(3-chloro-5-trifluoromethylpyridyl-2-oxy)-phenylcarbamoyl]-barbituric acid.

Suitable salts of the compounds of the formula I include, for example, the metal, ammonium or amine salts such as, for example, sodium, potassium, calcium, zinc, aluminum, iron$^{III}$, ammonium or alkylamine salts. Preferred are the calcium, zinc, aluminum and iron$^{III}$ salts and particularly the triethylamine salts.

In accordance with formula I, alkyl as an independent group and also as a moiety of a group of $R_1$ to $R_5$ is to be understood as meaning linear and branched-chain alkyl. This includes the methyl and ethyl groups and also the isomers of the propyl, butyl and pentyl groups. Cycloalkyl is to be understood as meaning cyclopropyl, cyclobutyl, cyclopentyl and cyclohexyl groups. Halogen is fluorine, chlorine, bromine or iodine, in particular fluorine or chlorine. The number of halogen atoms in the abovementioned halogenoalkyl radicals is 1 to 5, in particular 3.

5-Phenylcarbamoylbarbituric acid derivatives are described in European Patent Application No. 7,541 as insecticides and as inhibitors of the development of insects. They have the following general formula:

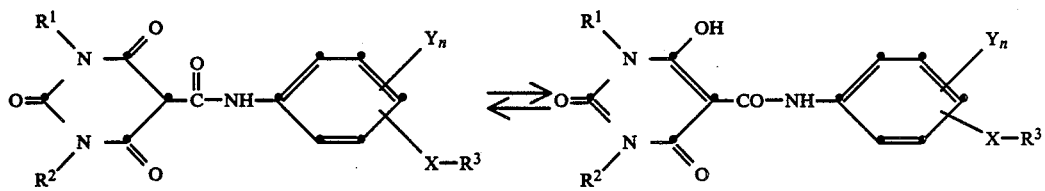

in which $R^1$ is H or alkyl, $R^2$ is H or alkyl, $R^3$ is halogenoalkyl or phenyl which is substituted by halogenoalkyl, X is O or S, Y is halogen or halogenoalkyl, n is 0, 1 or 2 and X, $R^3$ and Y in the ortho-position in relation to one another are also, collectively, the group —O—CF$_2$—O—CF$_2$—.

The novel active compounds, according to the invention, of the formula I differ structurally in a characteristic manner from the barbituric acid derivatives which are known from European Laid-Open Specification No. 7,541. In addition, it has been found, surprisingly, that the novel compounds have a more favourable spectrum of action against helminths which are parasitic in the animal organism, in particular in mammals. Thus they can be used with good results against nematodes, cestodes and trematodes. They are distinguished in this respect particularly by the fact that they are also completely effective against benzimidazole-resistant species, in particular against thiobendazole-resistant species, "thiabendazole" being understood as meaning the active compound 2-[4-thiazolyl]-benzimidazole.

The active compounds of the formula I are prepared by reacting: (a) an ester of the formula II

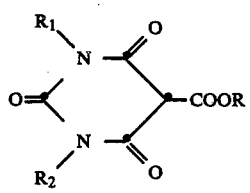

with an aniline derivative of the formula III

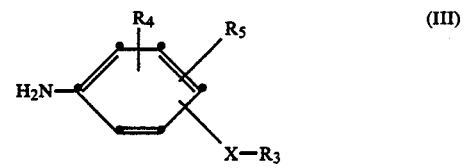

in which R is a lower alkyl group or a phenyl group which is unsubstituted or substituted by nitro, and the radicals $R_1$ to $R_5$ and X are as defined under formula I or (b) a substituted barbituric acid of the formula IV

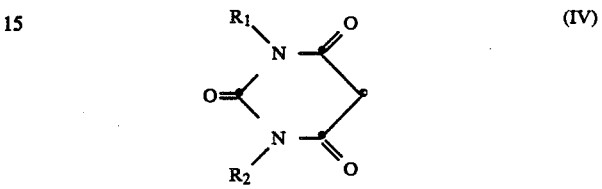

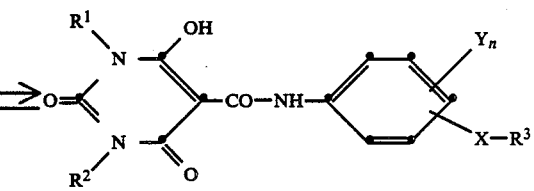

with a substituted phenyl isocyanate of the formula V

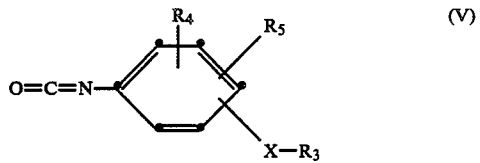

in which the radicals $R_1$ to $R_5$ and X are as defined under formula I, or (c) a substituted barbituric acid of the formula IV with a substituted benzoyl azide of the formula VI

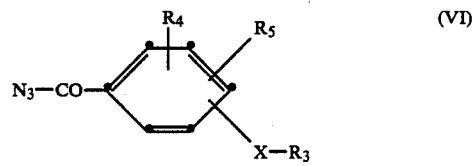

in which the radicals $R_1$ to $R_5$ and X are as defined under formula I.

The preparation variants (a) and (c) are carried out at reaction temperatures between 50° and 250° C. preferably 70° to 220° C. Variant (b) requires reaction temperatures between 0° and 220° C., in particular 0° to 200° C. Reactions (a), (b) and (c) can be carried out under normal or elevated pressure and in the absence or, preferably, in the presence of inert solvents or diluents, it being advantageous in some cases to carry out the reaction with a base.

Suitable bases are organic and inorganic bases; for example, preferably tertiary amines, such as trialkylamine (trimethylamine, triethylamine, tripropylamine and the like), pyridine and pyridine bases (for example 4-dimethylaminepyridine, 4-pyrrolidylaminopyridine and the like), picolines and lutidines, and also oxides, hydroxides, carbonates and bicarbonates of alkali and alkaline earth metals (for example CaO, BaO, NaOH, KOH, Ca(OH)$_2$, KHCO$_3$, NaHCO$_3$, Ca(HCO$_3$)$_2$, K$_2$CO$_3$, Na$_2$CO$_3$ and the like) and also acetates, for example CH$_3$COONa or CH$_3$COOK. Additional suitable bases are also alkali metal alcoholates; for example sodium ethylate, sodium propylate, potassium tert.-butylate or sodium methylate. It is advantageous to employ the base in 10 to 100% of the equimolar amount relative to the reactants.

The preparation of pharmaceutically acceptable salts, according to the invention, of compounds of the formula I is effected by neutralising the free acid in a customary manner with a base, in particular a physiologically acceptable base, which bases are suitable for forming, for example, metal, ammonium or amine salts comprising calcium, zinc, aluminum, iron$^{III}$, ammonium, alkali metal salts such as sodium, potassium or lithium salts, and further trialkylamine salts, for example the triethylamine salt, which is preferred. The bases mentioned above are appropriate for the preparation of salts according to the invention. The neutralisation is carried out in a polar solvent which is inert to the reaction, for example an alkanol or ester or an ether-like compound.

The free acid of the formula I results in the salts, which also form part of the invention, as a result of being reacted with bases.

Examples of solvents or diluents which are suitable for the preparation of the active substances according to the invention are ethers and ether-like compounds, such as dialkyl ethers (diethyl ether, diisopropyl ether, tert.-butyl methyl ether and the like), anisol, dioxane or tetrahydrofuran; aliphatic and aromatic hydrocarbons, such as benzene, toluene or petroleum ether; halogenated hydrocarbons, such as chlorobenzene, methylenechloride, chloroform, ethylenechloride, carbon tetrachloride or tetrachloroethylene; nitriles, such as acetonitrile or propionitrile; N,N-dialkylated amides, such as dimethylformamide; dimethyl sulfoxide; ketones, such as acetone, diethyl ketone and methyl ethyl ketone, and mixtures of such solvents with one another.

It can be advantageous in some cases if the reaction is carried out under an atmosphere of a protective gas. Examples of suitable protective gases are nitrogen, helium, argon or carbon dioxide.

The starting materials mentioned in the preparation variants (a), (b) and (c) are known (see, for example, Chem. Ber. 54, 1038 [1921]) or can be prepared analogously to the known substances.

The process of preparation described, including all the variants (a), (b) and (c) is a part of the present invention.

The active compounds, according to the invention, of the formula I can exist in various tautomeric forms, namely in the keto or enol form or in a mixture of keto and enol forms. This invention relates both to the individual tautomers and to mixtures thereof, and also to the salts of each of these forms and to the preparation thereof.

The invention also includes a process for prophylactically protecting animals against parasitic helminths, which comprises administering the active compounds of the formula I or the active compound formulations to the animals as an additive to their feed or drinks, or orally in a solid or liquid form, by injection or by means of the pour on method.

In every one of the processes, according to the invention, for controlling helminths or in every one of the anthelmintic compositions according to the invention, it is possible to employ the active compounds of the formula I in all their tautomeric forms or mixtures thereof or in the form of their salts.

Amongst the endoparasites which occur in warm-blooded animals, the helminths, in particular, cause considerable damage. Thus, for example, animals infested by these parasites exhibit not only retarded growth, but in some cases even damage which can result in mortality. It is therefore very important to develop therapeutic compositions which are suitable for controlling helminths and their development stages and for prophylaxis against attack by these parasites. Worm diseases which are particularly dangerous are those which are caused by nematodes, cestodes and trematodes parasitic in the gastro-intestinal tract and other organs, and which occur, in particular, in ruminants, such as sheep, cattle and goats, and also in horses, pigs, red deer, dogs, cats and poultry.

The damage caused by helminthiases can be considerable if the worm diseases occur in herds of cattle in a chronic manner and, in particular, in an epidemic manner. They manifest themselves, inter alia, in reductions in productivity, weakened resistance and increased mortality. The control and prophylaxis of helminthiases therefore rank as an urgent task, in order to avoid or reduce damage of this kind, which is, in particular, of economic importance.

In the present description, the term "helminths" is to be understood as meaning especially parasitic worms belonging to the phyla platyhelminthes (cestodes and trematodes) and nemathelminths (nematodes and related organisms), i.e. tapeworms, trematodes and round worms of the gastrointestinal tract and other organs (for example liver, lungs, kidneys, lymph vessels, blood etc.). Admittedly, a number of substances having an anthelmintic action are known, and these have been suggested for controlling the various species of helminths. However, these substances are not capable of giving full satisfaction, either because it is not possible to utilise their spectrum of action fully at a tolerable dosage, or because they exhibit undesirable side effects or properties in therapeutically effective doses. In this connection, an increasingly important part is also played by the resistance to certain classes of substances which nowadays occurs more frequently. "Albendazole", which is, for example, described in the literature (British Patent No. 1 464 326; Am. J. Vet. Res. 38, 1425–1426 (1977); Am. J. Vet. Res. 37, 1515–1516 (1976); Am. J. Vet. Res. 38, 807–808 (1977) and Am. J. Vet. Res. 38, 1247–1248 (1977), admittedly has a limited spectrum of anthelmintic action in ruminants. However, its action against benzimidazole-resistant nemstodes and adult liver flukes is insufficient, and, in particular, the pathologically important immature migratory forms of the latter are not attacked at dosages which are tolerable for the host animal.

It has now been found, surprisingly, that the active compounds of the formula I have an intense anthelmintic activity with a broad spectrum of action against nematodes, cestodes and trematodes and also have, in addition, a favourable toxicity to warm-blooded animals.

The novel active compounds, according to the invention, of the formula I are suitable, for example, for controlling parasitic nematodes of the orders (as classified by K. I. Skrajabin):
- Rhabditida
- Ascaridida
- Spirurida
- Trichocephalida or for controlling cestodes of the orders (as classified by Wardle & McLeod):
- Cyclophyllidae
- Pseudophyllidae or for controlling trematodes of the order:
- Digenea in domestic animals and productive livestock, such as cattle, sheep, goats, horses, pigs, cats, dogs and poultry. They can be administered to the animals either as an individual dose or repeatedly, individual doses being preferably between 1 and 500 mg per kg of body weight, depending on the species of animal. In some cases an improved action is achieved, or it is possible to manage with lower total doses, as a result of a protracted administration.

The compositions according to the invention are prepared by bringing the active compounds of the formula I into contact with liquid and/or solid formulation adjuncts by stepwise mixing and/or grinding in such a way that an optimum development of the anthelmintic activity of the formulation, corresponding to the application, is achieved.

The formulation stages can be supplemented by kneading, granulating (granules) and, if appropriate, compressing (pellets).

For protracted administration the active compounds of formula I can be administered in the form of controlled release boluses of the metal capsule type or the plastic, wing capsule type. Osmotic or mechanical, eroding or leaking forces can be used for ths controlled release of the active substances.

Examples of formulation adjuncts which are used are solid carriers, solvents and, if appropriate, surface-active substances (surfactants).

The following formulation adjuncts are used for preparing the compositions according to the invention:

Solid carriers, such as, for example, kaolin, talc, bentonite, sodium chloride, calcium phosphate, carbohydrates, cellulose powder, cotton seed flour and polyethylene glycol ethers, if appropriate binders, such as, for example, gelatine and soluble cellulose derivatives, if desired with the addition of surface-active substances, such as ionic or nonionic dispersing agents; also natural ground minerals, such as calcite, montmorillonite or attapulgite. It is also possible to add highly disperse silica or highly disperse absorbent polymers in order to improve the physical properties. Suitable particulate, adsorptive granular carriers are porous types, such as, for example, pumice stone, broken brick, sepiolite or bentonite, while examples of suitable non-sorptive carriers are calcite or sand. In addition, it is possible to use a large number of pregranulated materials of an inorganic or organic nature, such as, in particular, dolomite or comminuted plant material.

The following are suitable as solvents: aromatic hydrocarbons, preferably the fractions from $C_8$ to $C_{12}$, for example mixed xylenes or substituted naphthalenes, and phthalic acid esters, such as dibutyl or dioctyl phthalate; aliphatic hydrocarbons, for example cyclohexane or paraffins, alcohols and glycols and also ethers and esters thereof, for example ethanol, ethylene glycol or ethylene glycol monomethyl or monoethyl ether, ketones, for example cyclohexanone, strongly polar solvents, for example N-methyl-2-pyrrolidone, dimethyl sulfoxide or dimethylformamide, and vegetable oils which can be epoxidised, for example epoxidised coconut oil or soya oil, and water.

Depending on the nature of the active compound of the formula I to be formulated, suitable surface-active compounds are nonionic, cationic and/or anionic surfactants having good emulsifying, dispersing and wetting properties. Surfactants are also to be understood as meaning mixtures of surfactants.

Suitable anionic surfactants can be so-called water-soluble soaps as well as water-soluble synthetic surface-active compounds.

Suitable soaps are the alkali metal salts, alkaline earth metal salts or substituted or unsubstituted ammonium salts of higher fatty acids ($C_{12}$–$C_{22}$), for example the Na or K salts of oleic or stearic acid, or of natural mixtures of fatty acids, which can be obtained, for example, from coconut oil or tallow oil.

Frequently, however, so-called synthetic surfactants are used, in particular fatty sulfonates, fatty sulfates, sulfonated benzimidazole derivatives or alkylsulfonates.

The fatty sulfonates or sulfates are, as a rule, in the form of alkali metal salts, alkaline earth metal salts or substituted or unsubstituted ammonium salts and contain an alkyl radical having 8 to 22 C atoms, in which connection alkyl also includes the alkyl moiety of acyl radicals, for example the Na or Ca salt of ligninsulfonic acid, of dodecylsulfuric acid ester or of a mixture of fatty alcohol sulfates prepared from natural fatty acids. These products also include the salts of the sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Examples of alkylarylsulfonates are the Na, Ca or triethanolamine salts of dodecylbenzenesulfonic acid, of dibutylnaphthalenesulfonic acid or of a naphthalenesulfonic acid formaldehyde condensation product.

Furthermore, corresponding phosphates, for example salts of the phosphoric acid ester of a p-nonylphenol-(4-14)-ethylene oxide adduct, are also suitable.

Suitable nonionic surfactants are primarily polyglycol ether derivatives of aliphatic or cycloaliphatic alcohols, saturated or unsaturated fatty acids and alkylphenols, and these derivatives can contain 3 to 30 glycol ether groups and 8 to 20 carbon atoms in the (aliphatic) hydrocarbon radical and 6 to 18 carbon atoms in the alkyl radical of the alkylphenols.

Further suitable nonionic surfactants are the water-soluble adducts, containing 20 to 250 ethylene glycol ether groups and 10 to 100 propylene glycol ether groups, of polyethylene oxide with polypropylene glycol, ethylenediaminopolypropylene glycol and alkylpolypropylene glycol having 1 to 10 carbon atoms in the alkyl chain. The said compounds usually contain 1 to 5 ethylene glycol units per unit of propylene glycol.

Examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylenesorbitan, such as polyoxyethylenesorbitan trioleate, are also suitable.

The cationic surfactants are, in particular, quaternary ammonium salts which contain, as N-substituents, at least one alkyl radical having 8 to 22 C atoms and, as further substituents, lower, optionally halogenated alkyl radicals, benzyl radicals or lower hydroxyalkyl radicals. The salts are preferably in the form of halides, methylsulfates or ethylsulfates, for example stearyltrimethylammonium chloride or benzylidi-(2-chloroethyl)-ethylammonium bromide.

The surfactants which are customary in the technology of formulation are described, inter alia, in the following publications:

"McCutcheon's Detergents and Emulsifiers Annual", MC Publishing Corp., Ridgewood, N.J., 1980; Sisley and Wood, "Encyclopedia of Surface Active Agents", Chemical Publishing Co, Inc., New York, 1980.

Suitable binders for tablets and boluses are chemically modified, water-soluble or alcohol-soluble, polymeric natural materials, such as starch, cellulose or protein derivatives (for example methylcellulose, carboxymethylcellulose, ethylhydroxyethylcellulose and proteins, such as zein, gelatine and the like) and also synthetic polymers, for example polyvinyl alcohol, polyvinylpyrrolidone etc. The tablets also contain fillers (for example starch, microcrystalline cellulose, sugars, lactose etc.), lubricants and disintegrators.

If the anthelmintic compositions are in the form of feed concentrates, the carriers used are, for example, production rations, feed cereals or protein concentrates. In addition to the active compounds, such feed concentrates or animal feeds can also contain additives, vitamins, antibiotics, chemotherapeutic agents or other pesticides, especially bacteriostatic agents, fungistatic agents or coccidiostatic agents, or hormone preparations, substances which have an anabolic action or promote growth or affect the quality of the meat of animals for slaughter, or contain substances beneficial to the organism in other ways. If the compositions or the active compounds of the formula I present therein are added directly to the feed or to the cattle drink, it is preferable for the finished feed or the finished drink to contain the active compounds in a concentration of about 0.0005 to 0.02% by weight (5-200 ppm).

The administration of the compositions according to the invention to the animals to be treated can be effected perorally, parenterally, subcutaneously or topically, the compositions being in the form of solutions, emulsions, suspensions (drenches), powders, tablets, boluses and capsules.

As a rule, the anthelmintic compositions according to the invention contain 0.1 to 99% by weight, in particular 0.1 to 95% by weight, of an active compound of the formula I, 99.9 to 1% by weight, in particular 99.8 to 5% by weight, of a solid or liquid additive including 0 to 25% by weight, in particular 0.1 to 25% by weight, of a surfactant.

Whereas concentrated compositions are more likely to be preferred as commercial products, as a rule the final consumer uses dilute compositions.

Compositions of this type can also contain further additives, such as stabilisers, anti-foaming agents, viscosity regulators, binders, tackifiers and also other active compounds for achieving special effects.

Anthelmintic compositions of this type, used by the final consumer, also form a part of the present invention.

The following examples serve to illustrate the invention in greater detail, without limiting it.

1. PREAPARATION EXAMPLES

1.1
1,3-Dimethyl-5-[4-(3,5-dichloropyridyl-2-oxy)-phenylcarbamoyl]-barbituric acid 1.60 g (0.007 mol) of 1,3-dimethyl-5-ethoxycarbonylbarbituric acid and 1.79 g (0.007 mol) of 4-(3,5-dichloropyridyl-2-oxy)aniline are suspended in 25 ml of toluene and heated at reflux temperature for 16 hours, ethanol being evolved. After cooling, the precipitate is filtered off, washed with ethanol and dried. Yield: 2.7 g (89% of theory), melting point 234°-235° C.

1.2
1,3-Dimethyl-5-[4-(5-trifluoromethylpyridyl-2-oxy)-phenylcarbamoyl]-barbituric acid 1.60 g (0.007 mol) of 1,3-dimethyl-5-ethoxycarbonylbarbituric acid and 1.75 g (0.007 mol) of 4-(5-trifluoromethylpyridyl-2-oxy)-aniline are suspended in 20 ml of toluene and heated at reflux temperature for 16 hours, ethanol being evolved. After cooling, the precipitate is filtered off, washed with ethanol and dried. Yield: 2.7 g (89% of theory), melting point 180°-181° C.

1.3
1,3-Dimethyl-5-[4-(5-trifluoromethylpyridyl-2-oxy)-phenylcarbamoyl]-barbituric acid 11.41 g (0.050 mol) of 1,3-dimethyl-5-ethoxycarbonyl-barbituric acid and 12.7 g (0.050 mol of 4-(5-trifluoromethylpyridyl-2-oxy)-aniline are suspended in 200 ml of ethanol and 15 ml of dimethylformamide and heated at reflux temperature for 18 hours under a stream of protective gas (nitrogen). After cooling, the precipitate is filtered off, washed with acetone and dried. Yield: 19.5 g (90% of theory), melting point 180°-181° C.

1.4
1,3-Dimethyl-5-[4-(3,5-dichloropyridyl-2-oxy)-phenylcarbamoyl]-barbituric acid 7.8 g (0.050 mol) of 1,3-dimethylbarbituric acid and 14.0 g (0.050 mol) of 4-(3,5-dichloropyridyl-2-oxy)-phenyl isocyanate are suspended in 50 ml of xylene, and 1 g (0.010 mol) of triethylamine is added dropwise. The temperature rises to 45° to 50° C. After a further 50 ml of xylene have been added, the mixture is stirred at this temperature for 18 hours. ⅓ of the xylene is then distilled off. After cooling, the precipitate is filtered off, washed with xylene, suspended several times in 1 N HCl and then thoroughly washed with water and dried.

1.5
1,3-Dimethyl-5-[4-(3,5-dichloropyridyl-2-oxy)-phenylcarbamoyl]-barbituric acid 1.56 g (0.01 mol) of 1,3-dimethylbarbituric acid are added to a solution of 4.0 g (0.01 mol) of 4-(3,5-dichloropyridyl-2-oxy)benzoyl azide in 50 ml of toluene. A solution of 0.02 g (0.002 mol) of triethylamine in 5 ml of toluene is then added dropwise at room temperature. The mixture is then stirred for 1 hour at 50° C. and the temperature is then increased in stages of 20° C. each until reflux temperature has been reached. The reflux temperature is maintained until the evolution of nitrogen is complete. After cooling, the precipitate which has been deposited is filtered off, washed with ethanol, suspended several times in 1 N HCl and then thoroughly washed with water and dried. Yield: 4 g (85% of theory), melting point 234°-235° C.

The benzoyl azide employed as the precursor preparation is prepared as follows: 6.7 g (0.024 mol) of 3,5-dichloropyridyl-2-oxybenzoic acid in 40 ml of acetone are treated at 0° C. with 3.4 g (0.031 mol) of ethyl chloroformate in the presence of 2.9 g (0.028 mol) of triethylamine, and 2.4 g (0.036 mol) of sodium azide in 8 ml of water are also added to the mixture. After being stirred for 3 hours at 0° C., the mixture is poured into 100 ml of water and extracted with 60 ml of toluene. The toluene phase is separated off, dried over sodium sulfate at 0° C. and, after filtration, used for the reaction described above.

1.6
1,3-Dimethyl-5-[4-(3,5-dichloropyridyl-2-oxy)-phenyl-carbamoyl]-barbituric acid 1 g (0.010 mol) of triethylamine is added dropwise to a suspension of 7.8 g (0.050 mol) of 1,3-dimethylbarbituric acid and 18.0 g (0.050 mol) of 4-(3,5-dichloropyridyl-2-oxy)-benzoyl azide in 50 ml of xylene. The temperature rises to 45° to 50° C. After a further 50 ml of xylene have been added, the mixture is stirred at this temperature for 18 hours. ⅓ of the xylene is then distilled off. After cooling, the precipitate is filtered off, washed with xylene, suspended several times in 1 N HCl and then thoroughly washed with water and dried. Yield: 19.0 g (85% of theory), melting point 234°-235° C.

TABLE 1

Compounds of the formula

| Compound No. | $R_1$ | $R_2$ | $R_4$ | $R_5$ | X | $R_3$ | Physical constant [°C.] |
|---|---|---|---|---|---|---|---|
| 1.1 | $CH_3$ | $CH_3$ | H | H | O | (2)-Pyridyl-$Cl_2$(3,5) | m.p. 235-236 |
| 1.2 | $CH_3$ | $CH_3$ | H | H | O | (2)-Pyridyl-$CF_3$(5) | m.p. 178 (decomp.) |
| 1.3 | $CH_3$ | $CH_3$ | 3-Cl | 5-Cl | O | (2)-Pyridyl-Cl(3)-$CF_3$(5) | m.p. 205-206 |
| 1.4 | $CH_3$ | $CH_3$ | 3-Cl | 5-Cl | O | (2)-Pyridyl-$CF_3$(5) | m.p. 232-233 |
| 1.5 | $CH_3$ | $CH_2-CH=CH_2$ | H | H | O | (2)-Pyridyl-$CF_3$(5) | m.p. 105-107 |
| 1.6 | $CH_3$ | Cyclopropyl | H | H | O | (2)-Pyridyl-$CF_3$(5) | m.p. 142-144 |
| 1.7 | $CH_3$ | $CH_3$ | H | H | O | (5)-Pyridyl-Cl(4)$CF_2CCl_2$F(2) | |
| 1.8 | $CH_3$ | $CH_3$ | 3-Cl | H | O | (2)-Pyridyl-Cl(3)$CF_2CCl_2$F(5) | |
| 1.9 | $CH_3$ | $CH_3$ | H | H | O | (2)-Pyridyl-Cl(3)$CF_2CClF_2$(5) | |
| 1.10 | $CH_3$ | $CH_3$ | 2-$CH_3$ | 6-$CH_3$ | O | (2)-Pyridyl-Cl(3)$CF_3$(5) | |
| 1.11 | $CH_3$ | $CH_3$ | H | H | O | (2)-Pyridyl-Cl(3)$CF_3$(5) | m.p. 165-166 |
| 1.12 | $CH_3$ | $CH_3$ | 2-$C_3H_7$—iso | H | O | (2)-Pyridyl-$CF_3$(5) | m.p. 180-181 |
| 1.13 | $CH_3$ | $CH_3$ | 2-$CH_3$ | 6-$CH_3$ | O | (2)-Pyridyl-$CF_3$(5) | m.p. 191-194 |
| 1.14 | $CH_3O$ | $CH_3$ | H | H | O | (2)-Pyridyl-$Cl_2$(3,5) | m.p. 234-235 |
| 1.15 | $CH_3O$ | $CH_3$ | H | H | O | (2)-Pyridyl-Cl(3)$CF_3$(5) | m.p. 171-174 |
| 1.16 | $CH_3O$ | $CH_3$ | H | H | O | (2)-Pyridyl-$CF_3$(5) | m.p. 129-130 |
| 1.17 | $CH_3O$ | $CH_3O$ | H | H | O | (2)-Pyridyl-$Cl_2$(3,5) | m.p. 241-243 |
| 1.18 | $CH_3O$ | $CH_3O$ | H | H | O | (2)-Pyridyl-Cl(3)-$CF_3$(5) | m.p. 173-176 |
| 1.19 | $CH_3$ | $CH_3$ | 3-$OCH_3$ | H | O | (2)-Pyridyl-$Cl_2$(3,5) | m.p. 216-217 |
| 1.20 | $CH_3O$ | $CH_3$ | 3-$OCH_3$ | H | O | (2)-Pyridyl-$Cl_2$(3,5) | m.p. 171-172 |
| 1.21 | $CH_3$ | $CH_3$ | 2-$CH_3$ | 6-$CH_3$ | O | (2)-Pyridyl-$Cl_2$(3,5) | m.p. 251-253 |
| 1.22 | $CH_3$ | $CH_3$ | H | H | O | (2)-Pyridyl-$Cl_2$(3,5), $N(CH_2H_5)_3$ salt | m.p. 100-105 |
| 1.23 | $CH_3$ | $CH_3$ | H | H | O | (2)-Pyridyl-$Cl_2$(3,5), Ca salt | m.p. 257-260 |
| 1.24 | $CH_3$ | $CH_3$ | H | H | O | (2)-Pyridyl-$Cl_2$(3,5), Zn salt.$H_2O$ | m.p. 282-286 |
| 1.25 | $CH_3$ | $CH_3$ | H | H | O | (2)-Pyridyl-$Cl_2$(3,5), Al salt.$H_2O$ | m.p. 190-195 |
| 1.26 | $CH_3$ | $CH_3$ | H | H | O | (2)-Pyridyl-$Cl_2$(3,5), $Fe^{III}$ salt | m.p. 156-158 |
| 1.27 | $CH_3$ | $CH_3$ | H | H | O | (2)-Pyridyl-Cl(5)-F(3) | m.p. 188-189 |
| 1.28 | $CH_3$ | $CH_3$ | H | H | O | (2)-Pyridyl-CN(3)-$CH_3$(5)-$CF_3$(6) | m.p. 230-231 |
| 1.29 | $CH_3$ | $CH_3$ | H | H | O | (2)-Pyridyl-CN(3)-$CH_3$(4)-$CF_3$(6) | m.p. 211-213 |
| 1.30 | $CH_3$ | $CH_3$ | H | H | O | (2)-Pyridyl-CN(2)-$CF_3$(6) | m.p. 238-239 |
| 1.31 | $CH_3$ | $CH_3$ | 3-$OCH_3$ | H | O | (2)-Pyridyl-Cl(3)-$CF_3$(5) | m.p. 220-222 |
| 1.32 | $CH_3O$ | $CH_3$ | H | H | O | (2)-Pyridyl-Cl(5)-F(3) | m.p. 283-285 |
| 1.33 | $CH_3$ | $C_2H_5$ | H | H | O | (2)-Pyridyl-Cl(3)-$CF_3$(5) | |
| 1.34 | $CH_3O$ | $C_2H_5$ | H | H | O | (2)-Pyridyl-$Cl_2$(3,5) | |
| 1.35 | $CH_3$ | $CH_3$ | H | H | O | (5)-Pyridyl-$CF_3$(2) | m.p. 180-181 |
| 1.36 | $CH_3$ | $CH_3$ | H | H | O | (2)-Pyridyl-Cl(6)$CF_3$(4) | m.p. 174-176 |
| 1.37 | $CH_3O$ | $CH_3$ | H | H | O | (2)-Pyridyl-Cl(6)$CF_3$(4) | m.p. 165-168 |
| 1.38 | $CH_3$ | $CH_3$ | H | H | O | (2)-Pyridyl-$CF_3$(4) | m.p. 167-169 |
| 1.39 | $CH_3$ | $CH_3$ | H | H | O | (2)-Pyridyl-$CF_3$(4) Na Salt | m.p. 315-320 |
| 1.40 | $CH_3$ | $CH_2-CH=CH_2$ | H | H | O | (2)-Pyridyl-Cl(3)$CF_3$(5) | m.p. 119-120 |
| 1.41 | $CH_3$ | $CH_3$ | H | H | O | (2)-Pyridyl | m.p. 157-158 |
| 1.42 | $CH_3$ | $C_2H_5$ | H | H | O | (2)-Pyridyl-$Cl_2$(3,5) | m.p. 207-209 |
| 1.43 | $CH_3$ | $CH_2-CH=CH_2$ | H | H | O | (2)-Pyridyl-$Cl_2$(3,5) | m.p. 165-168 |
| 1.44 | $CH_3$ | $C_3H_7$—iso | H | H | O | (2)-Pyridyl-$Cl_2$(3,5) | m.p. 134-136 |

TABLE 2

Compounds of the formula

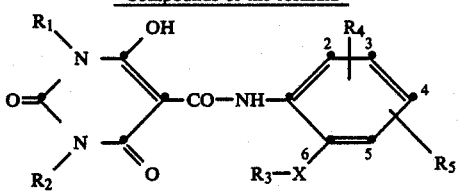

| Compound No. | $R_1$ | $R_2$ | $R_4$ | $R_5$ | X | $R_3$ | Physical constant [°C.] |
|---|---|---|---|---|---|---|---|
| 2.1 | $CH_3$ | $CH_3$ | 2-Cl | 3-Cl | O | (2)-Pyridyl | m.p. 241–242 |
| 2.2 | $CH_3$ | $CH_3$ | H | H | O | (2)-Pyridyl-$CF_3$(5) | |
| 2.3 | $CH_3$ | $C_2H_5$ | 4-$OCH_3$ | H | O | (2)-Pyridyl-Cl(3)-$CF_3$(5) | |

TABLE 3

Compounds of the formula

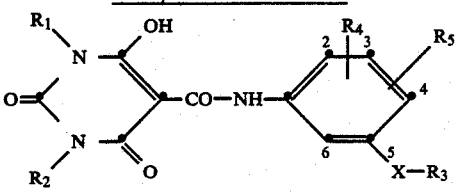

| Compound No. | $R_1$ | $R_2$ | $R_4$ | $R_5$ | X | $R_3$ | Physical constant [°C.] |
|---|---|---|---|---|---|---|---|
| 3.1 | $CH_3$ | $CH_3$ | H | H | O | (2)-Pyridyl-Cl(3)$CF_3$(5) | |
| 3.2 | $CH_3$ | $CH_3$ | 4-$CH_3$ | H | O | (2)-Pyridyl-Cl(3)$CF_3$(5) | |
| 3.3 | $CH_3$ | $CH_3$ | 4-$OCH_3$ | H | O | (2)-Pyridyl-Cl(3)$CF_3$(5) | m.p. 191–192 |
| 3.4 | $CH_3$ | $CH_3$ | 4-$OCH_3$ | H | O | (2)-Pyridyl-$Cl_2$(3,5) | m.p. 166–168 |
| 3.5 | $CH_3O$ | $CH_3$ | 4-$OCH_3$ | H | O | (2)-Pyridyl-$Cl_2$(3,5) | m.p. 182–185 |
| 3.6 | $CH_3$ | $CH_3$ | 4-$OCH_3$ | H | O | (2)-Pyridyl-$CF_3$(5) | m.p. 198–199 |
| 3.7 | $CH_3$ | $CH_3$ | 4-Cl | H | O | (2)-Pyridyl-Cl(3)-$CF_3$(5) | m.p. 194–195 |
| 3.8 | $CH_3$ | $CH_3$ | 4-$OCH_3$ | H | O | (2)-Pyridyl-Cl(5)-F(3) | m.p. 163–164 |
| 3.9 | $CH_3O$ | $CH_3$ | 4-$OCH_3$ | H | O | (2)-Pyridyl-Cl(3)-$CF_3$(5) | m.p. 163–165 |
| 3.10 | $CH_3O$ | $CH_3$ | 4-$OCH_3$ | H | O | (2)-Pyridyl-$CF_3$(5) | m.p. 165–167 |
| 3.11 | $CH_3$ | $C_2H_5$ | 4-$OCH_3$ | H | O | (2)-Pyridyl-$CF_3l$ (5) | |
| 3.12 | $CH_3$ | $CH_3$ | 4-$OCH_3$ | H | O | (2)-Pyridyl-Cl(6)$CF_3$(4) | m.p. 170–173 |

2. FORMULATION EXAMPLES (% = PERCENT BY WEIGHT)

| 2.1 Emulsion concentrates | (a) | (b) | (c) |
|---|---|---|---|
| Active compound from Tables 1 to 3 | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Mixed xylenes | 65% | 25% | 20% |

Emulsions of any desired concentration can be prepared from such concentrates by dilution with water.

| 2.2 Solutions | (a) | (b) | (c) | (d) |
|---|---|---|---|---|
| Active compound from Tables 1 to 3 | 80% | 10% | 5% | 95% |
| Ethylene glycol monomethyl ether | 20% | — | — | — |
| Polyethylene glycol MW 400 | — | 70% | — | — |
| NH—methyl-2-pyrrolidone | — | 20% | — | — |
| Epoxidised coconut oil | — | — | 1% | 5% |
| Petroleum ether (boiling range 160–190° C.) | — | — | 94% | — |

(MW = molecular weight)

The solutions are suitable for use in the form of very fine drops.

| 2.3 Granules | (a) | (b) |
|---|---|---|
| Active compound from Tables 1 to 3 | 5% | 10% |
| Kaolin | 94% | — |
| Highly disperse silica | 1% | — |
| Attapulgite | — | 90% |

The active compound is dissolved in methylene chloride, the solution is sprayed onto the carrier, and the solvent is then evaporated in vacuo. Granules of this type can be admixed to the cattle feed.

| 2.4 Dusts | (a) | (b) |
|---|---|---|
| Active compound from Tables 1 to 3 | 2% | 5% |
| Highly disperse silica | 1% | 5% |
| Talc | 97% | — |
| Kaolin | — | 90% |

Ready-to-use dusts are obtained by mixing the carriers intimately with the active compound.

| 2.5 Water-dispersible powder mixture | (a) | (b) | (c) |
|---|---|---|---|
| Active compound from Tables 1 to 3 | 25% | 50% | 75% |
| Na ligninsulfonate | 5% | 5% | — |

-continued

| 2.5 Water-dispersible powder mixture | (a) | (b) | (c) |
|---|---|---|---|
| Oleic acid | 3% | — | 5% |
| Na diisobutylnaphthalenesulfonate | — | 6% | 10% |
| Octylphenol polyethylene glycol ether (7-8 mol of ethylene oxide) | — | 2% | — |
| Highly disperse silica | 5% | 10% | 10% |
| Kaolin | 62% | 27% | — |

The active compound is thoroughly mixed with the additives, and the mixture is thoroughly ground in a suitable mill. This gives wettable powders which can be diluted with water to give suspensions of any desired concentration.

| 2.6 Emulsion concentrate | (a) | (b) | (c) |
|---|---|---|---|
| Active compound from Tables 1 to 3 | 10% | 8% | 60% |
| Octylphenol polyethylene glycol ether (4–5 mol of ethylene oxide) | 3% | 3% | 2% |
| Ca dodecylbenzenesulfonate | 3% | 4% | 4% |
| Castor oil polyglycol ether (35 mol of ethylene oxide) | 4% | 5% | 4% |
| Cyclohexanone | 30% | 40% | 15% |
| Mixed xylenes | 50% | 40% | 15% |

Emulsions of any desired concentration can be prepared from this concentrate by dilution with water.

| 2.7 Dust | (a) | (b) |
|---|---|---|
| Active compound from Tables 1 to 3 | 5% | 8% |
| Talc | 95% | — |
| Kaolin | — | 92% |

Ready-to-use dusts are obtained by mixing the active compound with the carrier and grinding the mixture on a suitable mill.

| 2.8 Granules | |
|---|---|
| Active compound from Tables 1 to 3 | 10% |
| Na ligninsulfonate | 2% |
| Carboxymethylcellulose | 1% |
| Kaolin | 87% |

The active compound is mixed and ground with the additives, and the mixture is moistened with water. This mixture is extruded and then dried in a stream of air.

| 2.9 Granules | |
|---|---|
| Active compound from Tables 1 to 3 | 3% |
| Polyethylene glycol (MW 200) | 3% |
| Kaolin | 94% |

(MW = molecular weight)

The active compound is finely ground and applied uniformly, in a mixer, to the kaolin, which has been moistened with polyethylene glycol. Dust-free coated granules are obtained in this manner.

| 2.10 Suspension concentrates | |
|---|---|
| Active compound from Tables 1 to 3 | 40% |
| Ethylene glycol | 10% |
| Nonylphenol polyethylene glycol ether (15 mol of ethylene oxide) | 6% |
| Na ligninsulfonate | 10% |
| Carboxymethylcellulose | 1% |
| 37% aqueous formaldehyde solution | 0.2% |

-continued

| 2.10 Suspension concentrates | |
|---|---|
| Silicone oil in the form of a 75% aqueous emulsion | 0.8% |
| Water | 32% |

The active compound is finely ground and intimately mixed with the additives. This gives a suspension concentrate from which suspensions of any desired concentration can be prepared by dilution with water.

| 2.11 Drenchsuspensions (subst. in g) | (a) | (b) | (c) | (d) |
|---|---|---|---|---|
| Active compound from Tables 1 to 3 | 2.5 | 5 | 10 | 20 |
| cellulose, microcristalline | 1.2 | 0.8 | — | 1.0 |
| Pluronic L 101 | — | — | — | 0.4 |
| Polysorbat 80 | 0.2 | — | — | — |
| Polyvinylpyrrolidone K 30 | — | 1 | 2 | — |
| Polyathyleneglycol 3000 | 5.0 | — | — | — |
| Glycerine PH 85% | 6.0 | 10.0 | — | — |
| Sodium carboxymethyl cellulose medium viscosity | — | — | 0.84 | 0.2 |
| Bentonite Standard | — | — | 0.9 | — |
| Methylparabene | 0.1 | 0.1 | 0.10 | 0.10 |
| Propylparabene | 0.02 | 0.02 | 0.02 | 0.02 |
| Benzoic acid | 0.1 | 0.1 | 0.1 | 0.1 |
| demineralized water ad 100 ml | q.s. | q.s. | q.s. | q.s. |

(q.s. quantum satis; sufficient quantity)

Preservatives are dissolved in hot water (preparation A). Suspension aids and viscosity enhancers are dispersed in water and active compounds and tensides added. This mixture is homogenized until a homogeneous suspension (preparation B) is obtained. Preparations A and B are combined together with the remaining water and finally homogenized.

| 2.12 Tablets or boluses | | |
|---|---|---|
| I | Active compound from Tables 1 to 3 | 33.0% |
| | Methylcellulose | 0.80% |
| | Highly disperse silica | 0.80% |
| | Maize starch | 8.40% |
| II | Crystalline lactose | 22.50% |
| | Maize starch | 17.00% |
| | Microcrystalline cellulose | 16.50% |
| | Magnesium stearate | 1.00% |

I  The methylcellulose is stirred into water and allowed to swell; the silica is stirred into the swollen mixture and is suspended homogeneously. The active compound and the maize starch are mixed. The aqueous suspension is incorporated into this mixture and kneaded to form a paste. This composition is granulated through a 12 m (mesh) sieve and dried.
II All the 4 adjuncts are thoroughly mixed.
III Phases I and II are mixed and compressed to give tablets or boluses.

3. BIOLOGICAL EXAMPLES

The anthelmintic activity is demonstrated by means of the following tests:

3.1 Test on sheep infested with nematodes, such as Haemonchus contortus and Trichostrongylus colubriformis The active compound is administered, by means of a probang or by injection into the rumen, in the form of a suspension, to sheep which have previously been artificially infested with nematodes, such as Haemonchus contortus and Trichostrongylus colubriformis. 1 to 3 animals are used per test or per dose. Each sheep is treated with only a single dose.

An initial evaluation is carried out by comparing the number of worm eggs excreted in the dung of the sheep before and after the treatment.

7 to 10 days after the treatment the sheep are killed and dissected. Evaluation is effected by counting the worms remaining in the intestine after the treatment. Sheep which have been infested at the same time and in the same way, but have not been treated, are used as a control or comparison.

Compared with untreated, but infested, comparison groups, sheep which have been treated with a suspension of an active compound from Tables 1 to 3 exhibit an attack by nematodes which is reduced by at least 90%, at a dose less than 20 mg/kg of body weight. In addition, compounds Nos. 1.12, 1.13, 1.20 and 3.3 are 95% effective at a dose of 12 mg/kg, compounds Nos. 1.1, 1.11, 1.14, 1.15, 1.16, 1.19, 1.27 and 1.32 are 95% effective at a dose of 5 mg/kg and compound No. 1.2 is 100% effective at a dose of 2.5 mg/kg. Compound No. 3.4 is 80 to 100%, compound No. 3.6 is 60 to 100% effective at a dose of 2.5 mg/kg of body weight.

What is claimed is:

1. A 5-phenylcarbamoylbarbituric acid compound of the formula I

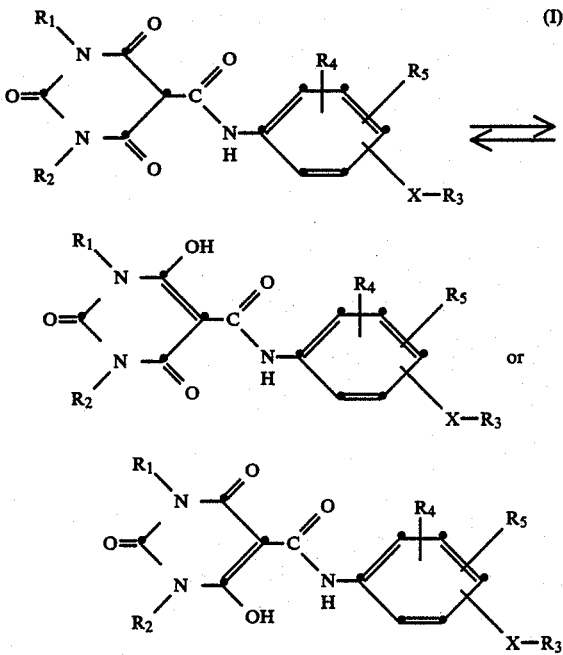

and tautomeric forms and salts thereof in which $R_1$ and $R_2$ independently of one another are $C_1$–$C_5$-alkyl, $C_1$–$C_3$-alkoxy, $C_3$–$C_6$-cycloalkyl, allyl or phenyl; $R_3$ is pyridyl which is unsubstituted or monosubstituted to trisubstituted by substituents selected from the group consisting of halogen, cyano, thiocyano, isothiocyano, $C_1$–$C_5$-alkanoyl, $C_1$–$C_5$-alkyl, $C_1$–$C_5$-halogenoalkyl, $C_1$–$C_5$-halogenoalkoxy, $C_1$–$C_5$-alkoxy or benzyl; $R_4$ and $R_5$ independently of one another are hydrogen, halogen, $C_1$–$C_5$-halogenoalkyl, $C_1$–$C_5$-alkyl, $C_1$–$C_5$-alkoxy or $C_1$–$C_5$-alkylthio; and X is oxygen or sulfur.

2. A compound according to claim 1, in which $R_1$ and $R_2$ independently of one another are $C_1$–$C_5$-alkyl, $C_1$–$C_3$-alkoxy, $C_3$–$C_6$-cycloalkyl or allyl; $R_3$ is pyridyl which is unsubstituted or monosubstituted to trisubstituted by substituents selected from the group consisting of halogen, cyano, thiocyano, isothiocyano, $C_1$–$C_5$-alkanoyl, $C_1$–$C_5$-alkyl, $C_1$–$C_5$-halogenoalkyl, $C_1$–$C_5$-halogenoalkoxy, $C_1$–$C_5$-alkoxy and benzyl; $R_4$ is hydrogen, halogen, $C_1$–$C_5$-halogenoalkyl, $C_1$–$C_5$-alkyl or $C_1$–$C_5$-alkoxy; $R_5$ is hydrogen, halogen, $C_1$–$C_5$-halogenoalkyl or $C_1$–$C_5$-alkyl; and X is oxygen or sulfur.

3. A compound according to claim 1, in which $R_1$ is $C_1$–$C_5$-alkyl or $C_1$–$C_3$-alkoxy; $R_2$ is $C_1$–$C_5$-alkyl, $C_1$–$C_3$-alkoxy, cyclopropyl or allyl; $R_3$ is pyridyl which is unsubstituted or mono- to trisubstituted by substituents selected from the group consisting of halogen, cyano, $C_1$–$C_5$-alkyl and $C_1$–$C_5$-halogenoalkyl; $R_4$ is hydrogen, halogen, $C_1$–$C_5$-alkyl or $C_1$–$C_5$-alkoxy; $R_5$ is hydrogen, halogen or $C_1$–$C_5$-alkyl; and X is oxygen; and metal salts or mono-, di- or trialkylamine salts thereof.

4. A compound according to claim 3, in which $R_1$ is methyl or methoxy; $R_2$ is methyl, ethyl, cyclopropyl or allyl; $R_3$ is (2)- or (5)-pyridyl, which is unsubstituted or mono- to trisubstituted by substituents selected from the group consisting of chlorine, fluorine, cyano, methyl, trifluoromethyl and 1,1-difluoro-2,2-dichloro-2-fluoroethyl; $R_4$ is hydrogen, chlorine, methyl, isopropyl or methoxy; $R_5$ is hydrogen, chlorine or methyl; and X is oxygen, and the Ca, Zn, Al, $Fe^{III}$ and triethylamine salts thereof.

5. A compound according to claim 4, in which $R_2$ is methyl, cyclopropyl or allyl.

6. A compound according to claim 5, in which $R_3$ is (2)-pyridyl which is unsubstituted or mono- to trisubstituted by substituents selected from the group consisting of chlorine, fluorine, cyano, methyl or trifluoromethyl.

7. A compound according to claim 6, in which $R_1$ is methyl or methoxy, $R_2$ is methyl, $R_3$ is (2)-pyridyl mono- or disubstituted by substituents selected from the group consisting of chlorine, fluorine and trifluoromethyl, $R_4$ is hydrogen, methyl, isopropyl or methoxy, $R_5$ is hydrogen or methyl and X is oxygen.

8. A compound according to claim 7, in which $R_4$ is hydrogen and $R_5$ is hydrogen and additionally, if $R_1$ is other than methoxy, $R_4$ is methoxy.

9. 1,3-Dimethyl-5-[4-(3,5-dichloropyridyl-2-oxy)-phenylcarbamoyl]-barbituric acid according to claim 7.

10. 1,3-Dimethyl-5-[4-(5-trifluoromethylpyridyl-2-oxy)-phenylcarbamoyl]-barbituric acid according to claim 7.

11. 1-Methoxy-3-methyl-5-[4-(3,5-dichloropyridyl-2-oxy)-phenylcarbamoyl]-barbituric acid according to claim 7.

12. 1,3-Dimethyl-5-[4-(3-chloro-5-trifluoromethylpyridyl-2-oxy)phenylcarbamoyl]-barbituric acid according to claim 7.

13. 1-Methoxy-3-methyl-5-[4-(3-chloro-5-trifluoromethylpyridyl-2-oxy)-phenylcarbamoyl]-barbituric acid according to claim 7.

14. 1,3-Dimethyl-5-[3-methoxy-4-(3,5-dichloropyridyl-2-oxy)-phenylcarbamoyl]-barbituric acid according to claim 7.

15. 1,3-Dimethyl-5-[4-methoxy-3-(3-chloro-5-trifluoromethylpyridyl-2-oxy)-phenylcarbamoyl]-barbituric acid according to claim 7.

16. 1,3-Dimethyl-5-[4-methoxy-3-(3,5-dichloropyridyl-2-oxy)-phenylcarbamoyl]-barbituric acid according to claim 7.

17. 1,3-Dimethyl-5-[4-methoxy-3-(5-trifluoromethylpyridyl-2-oxy)phenylcarbamoyl]-barbituric acid according to claim 7.

18. An anthelmintic composition which contains, as the active component an anthelmintically effective amount of, at least one compound of the formula I, a tautomer or a salt thereof according to claim 1 and also carriers and further adjuncts.

19. A process for controlling parasitic helminths, which comprises administering an anthelmintically effective amount of a compound of the formula I according to claim 1 to an animal.

* * * * *